United States Patent [19]
Freitag et al.

[11] Patent Number: 6,061,591
[45] Date of Patent: May 9, 2000

[54] ARRANGEMENT AND METHOD FOR DIAGNOSING MALIGNANT TISSUE BY FLUORESCENCE OBSERVATION

[75] Inventors: Lutz Freitag, Hemer; Franz Dankwart-Eder, Kist, both of Germany

[73] Assignee: Richard Wolf GmbH, Knittlingen, Germany

[21] Appl. No.: 08/824,649

[22] Filed: Mar. 24, 1997

[30] Foreign Application Priority Data

Mar. 29, 1996 [DE] Germany .............................. 196 12 536

[51] Int. Cl.$^7$ ........................................................ A61B 5/00

[52] U.S. Cl. ........................................... 600/476; 607/901

[58] Field of Search .................... 600/473–478; 607/901

[56] References Cited

U.S. PATENT DOCUMENTS 4,556,057  12/1985  Hiruma et al. ........................... 600/476
4,768,513   9/1988  Suzuki ..................................... 600/476

*Primary Examiner*—Ruth S. Smith
*Attorney, Agent, or Firm*—Akin, Gump, Strauss, Hauer & Feld, L.L.P.

[57] ABSTRACT

The invention relates to an arrangement and method for diagnosing malignant tissue by fluorescence observation with an endoscope. A stroboscope is used as a white light source in order to illuminate the interesting tissue region through the endosocope. A laser is simultaneously used in order to stimulate the fluorescence. At a time, the analyzer is activated in the dark phase between two light flashes of the stroboscope and deactivated during a visible light flash. The tissue, with a continuous fluorescence stimulation by exposure to light with a stimulating wavelength, may be observed under a pseudo-white light. The spectrogram may be represented on a screen which displays a normal white light endoscopic picture.

12 Claims, 3 Drawing Sheets

ARRANGEMENT AND METHOD FOR DIAGNOSING MALIGNANT TISSUE BY FLUORESCENCE OBSERVATION

BACKGROUND OF THE INVENTION

The invention relates on the one hand to an arrangement and on the other to a method for diagnosing malignant tissue by fluorescence observation using an endoscope which comprises a white light source, a fluorescence stimulator emiting a light beam, and an analyzer.

With endoscopic tumor diagnosis, one can differentiate between direct and indirect signs of tumors. A direct sign of a tumor can be recognized by the tumor mass itself. An indirect sign of a tumor is for example an irregular course of vessels. According to the picture of disease and disease stage of the tissue, however, the indirect sign of a tumor becomes less specific. Early cancers, that is X-ray negative tissue change and tissue change which can no longer be endoscopically differentiated from healthy tissue, may then only be diagnosed with difficulty. Here, one uses fluorescence examinations in order to determine in healthy surroundings, cell or tissue structures. With this, one evaluates the differing fluorescence behavior of healthy and diseased tissue. Apart from the measuring and evaluation of autofluorescence, it is also known to enhance the contrast by enrichment with photosensitive substances with a strong affinity to malignant tissue. Here, one is concerned with medication-induced fluorescence or photodynamic diagnostics. These substances are stored in malignant tissue longer than in the healthy surroundings. With light exposure in the ultra-violet to the infra-red region, which is usually produced by a laser, the fluorescence is stimulated. An analysis of the wave length of the fluorescence, which is emitted by the damaged tissue makes possible the diagnosis of tumors. The autofluorescence and the medication-induced fluorescence thus makes possible further information, which may not be determined with the naked eye.

U.S. Pat. No. 4,556,057 discloses means for carrying out an endoscopic tumor diagnosis including means for stimulating the fluorescence, for spectral analysis and the necessary laser apparatus. With this an endoscope with an optical fiber is introduced into a body cavity and the tissue to be examined is irradiated with a pulsating laser light. The fluorescence light induced is then measured and evaluated in order to determine whether a tissue is normal or diseased. Diseased tissue may then be destroyed by a high laser energy through the same optical fiber.

The examination is carried out in the monochromatic light spectrum, with which fluorescence can be stimulated. A picture may be drawn up of the diseased tissue. For this an image intensifier is necessary since the interesting fluorescence signal is several powers of ten lower than that which the naked eye can perceive.

A simultaneous observation with white light may not be carried out. In order to locally pinpoint possibly diseased tissue, a white light source is provided, which can be controlled alternately with the pulsed laser beam.

A simultaneous evaluation of the optically indirect tumor signs and the fluorescent tumor signs has not been possible up to now. This however would be desired, since for example dysplasia and inflammation have fluorescence. Furthermore the whole diagnosis procedure and the probing in the body cavity would be made easier or improved.

The known arrangement is also not suitable for examining tumors with autofluorescence, since the energy of the light used for fluorescence stimulation may not be limited. This is required because the cells lose the fluorescent ability when a monochromatic light for fluorescence stimulation of biological tissue exceeds a certain energy or intensity peak. The loss of fluorescent ability is called bleaching.

BRIEF SUMMARY OF THE INVENTION

It is therefore the object of the invention to provide an arrangement and to demonstrate a method through which the recognizing abilities of changed cell or tissue patterns with respect to healthy tissue can be improved by way of fluorescence examination, wherein at the same time, a normal optical image of the tissue to be examined can be observed with white light.

The crux of the invention forms the measure of applying a light source which produces white light and which comprises a device for the periodic intensity change of the light beam leaving the light source, whilst a continuous light beam is constantly emitted from the fluorescence stimulator. The intensity change may be effected by an interruption of the light beam as well as also by a control regulation of the light beam or the white light source.

The invention then so makes use of the known physical effect that the human eye composes a stationary image above the flicker limit and that this effect may also be applied to an image recording apparatus or a video chip. In this way, according to the invention, there results the advantage that the fluorescence which one wishes to analyze, even when it lies powers of ten below the visible light wavelength, may be observed. The threshold of visibility is then reduced.

Principally the white light can be produced by a white flashtube. It may however also be generated by the additive mixture of the three spectral colors red, green and blue.

During the diagnosis there constantly comes from the fluorescence stimulator a continuous light beam with a wavelength which stimulates the fluorescence of the tissue to be examined. Preferably this then concerns monochromatic light. Fundamentally however, a feeding with polychromatic light is possible.

By way of the change in intensity of the light beam leaving the white light source, a dark phase is extracted in the cycle which can be used for analyzing the wavelength of the fluorescence leaving the tissue. For analysis a spectrometer is usually applied. However, principally a camera for a full picture may also be employed.

The analyzer is logically so integrated into the arrangement according to the invention, that upon an intensity change of the light beam of the white light source tending towards zero, the analyser is activated and during a visible light pulse is deactivated. In this way, it is avoided that the analyzer is irradiated by a light pulse, through which it would not be useable for analysis for a certain time. Activation or deactivation of the analyzer is to be understood as a regulation of the sensitivity of the analyzer. The analyser must not be off in a deactivated phase but must merely be so reduced in its sensitivity that its functioning ability is not adversely affected by the light impulse. This may be effected by applying a suitable filter in series.

Thus according to the invention a continuous light source for fluorescence stimulation and a very intense ultra short white light source are combined, wherein the fluorescence analysis in the dark phase takes place between the impulses of white light.

According to one embodiment, the light source is a component of a stroboscope. The stroboscope is coupled onto the illumination beam and replaces the hitherto used continuous light. By way of the light pulse sequence with a high intensity of an extremely short duration, a white light image is produced with which the normal anatomical-physiological slightly reddened mucous membrane can be observed.

The tissue to be observed is illuminated by the stroboscope lamp with the cycle of the control frequency. With this, the control frequency is preferably higher than 15 Hz. The period of the light flash may lie between 1 μs and 100 μs according to the flashtube.

The stroboscope effect which also deceives the human eye, is likewise applicable to a video chip or to a video tube. The light pulses on the video chip or the video tube are of an extremely short duration. Between the light pulses of the white light there is a state of darkness. During this dark phase the fluorescence can be analyzed, since the fluorescence stimulator is always there. For the observer however there results a picture with pseudo-white light during the whole cycle time. With a ratio of the illumination phase to the dark phase of for instance 1:1000 there is a state of darkness in 99.9% of the whole phase, this being able to be used for analysis as fluorescent time. The deficit of sensitivity with the fluorescence analysis is thus compensated by the analysis time.

According to another embodiment, a laser is applied as a fluorescence stimulator. As such the laser may be a krypton or argon ion laser. The light emitted from the laser is to be chosen such that a good autofluorescence is stimulated. With a medication induced fluorescence, the light is to be matched to the respective medication.

Many laser materials may supply enhancement for a whole range of differing light frequencies. In order, in these cases, to hold a monochromatic emission on a desired wavelength, filters (prisms, grids, interference filters and others) must be applied to suppress other wavelengths. Since with the arrangement according to the invention the laser runs continuously, as a rule any wavelengths may be used. With a continuous variation of the passband wavelength of the applied filter, then broad bands of the spectrum may be covered with monochromatic light beaming without gaps.

The invention allows also the application of an arc lamp, for example a xenon or mercury vapor discharge lamp, as a fluorescence stimulator. With this, a light source is available with a very defined spectrum in the blue region. This light source is much cheaper than a laser.

A further embodiment applying further the teaching of the invention has a filter associated with the analyzer, this filter selectively blanking out the stimulation wavelength emitted from the fluorescence stimulator. With the filter, this may concern edge filters, interference filters, prisms, grid systems or others.

It is particularly advantageous that a system of at least two filters is incorporated on the stimulation side, i.e., in the light beam emitted from the fluorescence stimulator, as well as on the analysis side, wherein these filters are so mechanically or electronically coupled, that the wavelength of the fluorescence leaving the tissue, which corresponds to the stimulation wavelength, is selectively blended out before the analyzer. On application of an array spectrometer (OMA= optical multichannel analyzer) or also an interference spectrometer, the whole spectrum may then be analyzed simultaneously.

It is also possible that a spectrometer sensor on the analysis side can be directly coupled with the filter on the stimulation side. By coupling the filters on the stimulation and analysis sides, any light sources may then be used for diagnosis. Therefore, comparatively inexpensive light sources may be applied.

With the method for diagnosing malignant tissue by fluorescence observation according to the invention, a stroboscope is employed in order to observe the interesting region within a body cavity using an endoscope. The flash sequence frequency preferably lies above 15 Hz. Simultaneously, a monochromatic light source, for example an argon laser, is used in order to continuously stimulate the autofluorescence. The white light and the laser light may basically be coupled in the endoscope by one and the same optical fiber. It is of course also possible to employ separate optical fibers.

Due to the sequence of light flashes of a high intensity and an extremely short duration, a white light image is created. Between the individual flashes there results a comparatively long reading time for the video chip (CCD image sensor chip) or the video tube. The intensity difference between the signals coming from the white light and the signals coming from the fluorescent light is overcome by the differences in the observation and analysis time. The recorded spectrogram may then be indicated on a screen which a normal white light endoscope picture reproduces.

Due to the application of filters, which are logically so coupled that in each case, the wavelength coming from the tissue and corresponding to the stimulation wavelength is blanked out before the analyzer, it is possible, with a continuous variation of the passband wavelength, to cover broad ranges of the spectrum without gaps using monochromatic light irradiation (claim 7). The stimulation may then be effected with wavelengths in differing spectral regions, for example blue, yellow, red, etc.

Electronic or mechanical red-green-blue filters are well suited for the application with the arrangement or method according to the invention.

As a whole, by way of the arrangement and method according to the invention, the required examination time can be considerably reduced. Since a real image may be observed, the examination is essentially much simpler and more reliable.

Basically, according to the invention it is also possible instead of the previously described reflection of the tissue, to measure the absorption of the tissue. For this purpose the tissue is pierced. This may be effected once in that the optical fiber is pierced into the tissue and through which the laser beam is guided. In this case the whole tissue would be illuminated. By way of the differing absorption of healthy and diseased tissue, edges of tumors for example can be recognized more clearly. Furthermore it is also possible to pierce with the analysis fiber in order to directly measure the absorption.

The arrangement according to the invention may suitably be complemented with means for irradiating with high energy through the same optical fiber. With this, after diagnosis, a destruction or removal of the diseased tissue may be carried out. As such, the same laser may be used for diagnosing purposes as well as for the irradiation, when the laser energy can be adjusted accordingly.

BRIEF DESCRIPTION OF THE SEVERALS VIEWS OF THE DRAWING

The invention is hereinafter described by way of several embodiments shown in the drawings. These show:

FIG. 1 shows in a technically generalized representation, an arrangement for the diagnosis of malignant tissue by fluorescence observation, FIG. 2 is a schematic representation of the active and passive phases, running over a time period, of the laser, stroboscope, spectrometer and video chip, FIG. 3 shows a further embodiment form of an arrangement according to the invention, FIG. 4 shows a first filter wheel of the arrangement according to FIG. 3, FIG. 5 shows a second filter wheel of the arrangement according to FIG. 3, FIG. 6 shows an impulse diagram, FIG. 7 shows a further embodiment form of a filter wheel and FIG. 8 shows likewise, in a technically generalized representation, a further arrangement for the diagnosis of malignant tissue by fluorescence observation.

DETAILED DESCRIPTION OF THE INVENTION

Figure 1:
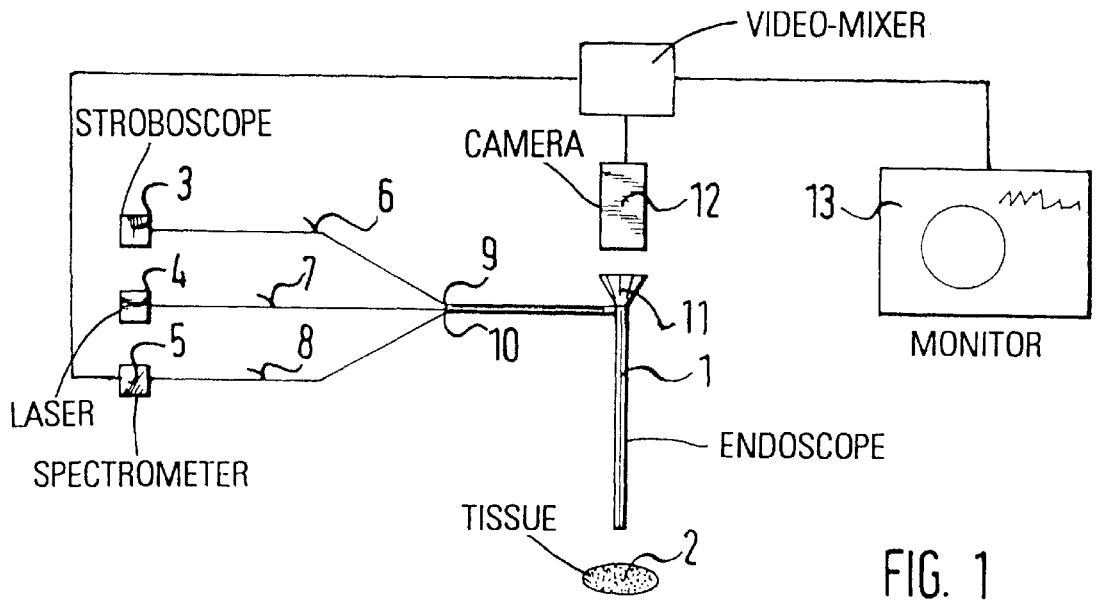

In FIG. 1, a flexible or rigid endosope is indicated at 1, this endoscope being introduced into a body cavity, not described in more detail, for examining the tissue 2.

Furthermore, a white light source in the form of a stroboscope 3, a laser 4 stimulating the fluorescence of the observed tissue 2 and a spectrometer 5 are shown. The connecting of the stroboscope 3, laser 4 and spectrometer 5 is technically illustrated more easily by way of lines 6, 7 and 8.

Basically, for the light guiding from the stroboscope 3 and laser 4 or to the spectrometer 5, a single optical fiber 9 is sufficient. A useful solution however lies in that light from the stroboscope 3 and the laser 4 is guided via a common optical fiber and a separate analysis fiber 10 is provided for the analysis.

During the diagnosis a continuous laser beam is constantly emitted from the laser 4 in order to stimulate the autofluorescence of the tissue 2. At the same time the stroboscope 3 is used in order to illuminate the interesting tissue 2 through the endoscope 1. With a corresponding choice of cycle frequency of the stroboscope 3, there is produced such a white light image corresponding to the normal anatomical physiological genuine picture. The analysis of the wavelength of the fluorescence leaving the tissue 2 is carried out using the spectrometer 5. For this purpose, the stroboscope 3 and the spectrometer 5 are logically so coupled and controllable, that in each case the spectrometer is activated in a dark phase and deactivated during a light flash.

The endoscope 1 has at its disposal an image sensor which permits representation on a screen. This allows the dismantling of the image projected by the objective and its conversion into electric signals. The electric signals are temporarily stored in intergrated memory-coupled components, before they are called up by high frequency cycle impulses and converted into video signals.

During the diagnosis the tissue to be examined may be observed through the eyepiece 11, this being either with the eye or via an endocamera 12 as a genuine picture. The recorded spectrogram can be shown on a screen 13 which normally reproduces a white light endoscopic picture.

The signal which is present after evaluation and editing by the spectrometer 5 may be mixed into the examination picture. It may also be given out in the form of an acoustic signal. The examiner then recognizes by way of the signal change, that there is an abnormality with tissue being examined. In a further form, it is provided that by way of permanent recording of the spectrum, a tissue pattern is determined which corresponds to the normal spectrum of the respective patient. If, during the course of the diagnosis, this individual pattern changes, a corresponding signal is emitted. The arrangement according to the invention then has a self-learning algorithm at its disposal.

Figure 2:
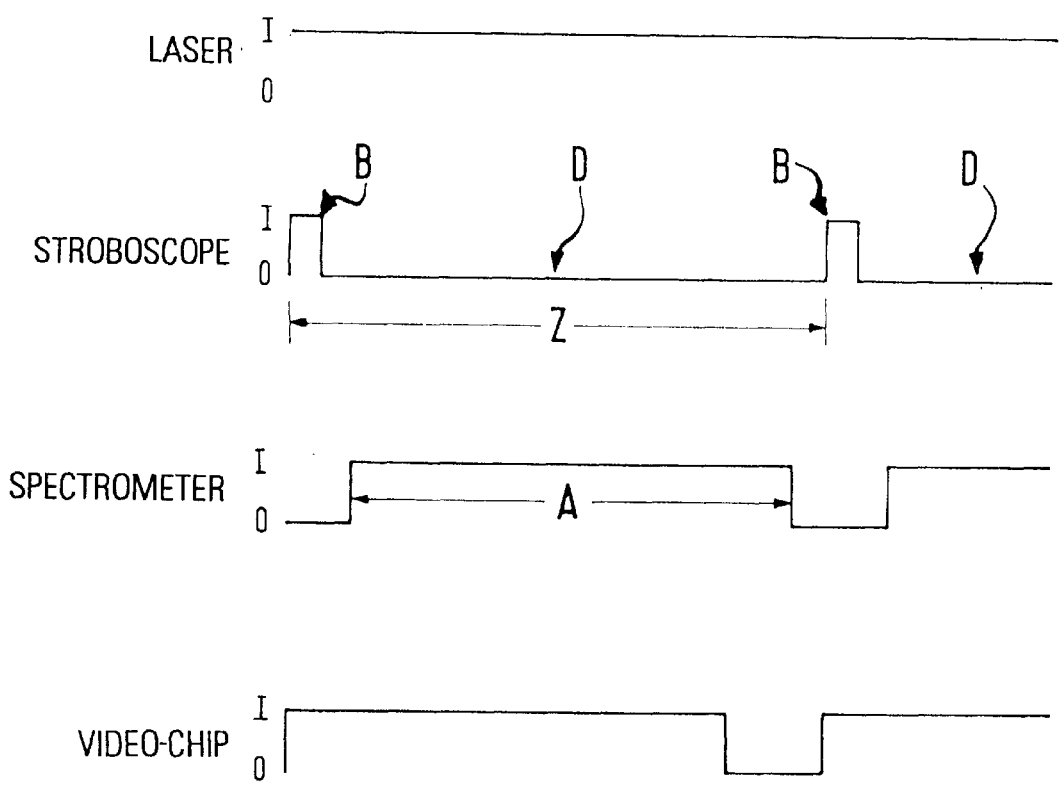

In FIG. 2 the active phases of the fluorescence stimulation by the laser, of the stroboscope, of the fluorescence analysis by the spectrometer and of the video chip are recognized in each case by the position (I), and the passive phases by the position (O).

From this it is clear that the laser continuously runs during the diagnosis in order to stimulate the autofluorescence of the tissue. The stroboscope is used in order to illuminate the interesting tissue region through the endoscope. In each case, in the dark phase D between two flashes B, the spectrometer is active. The dark phase D is available as an analysis time A because the laser is continuously connected. The video chip in each case is active at the beginning of a flash B and switches itself off shortly before the end of the analysis time. The electronic switching times are correspondingly taken into account with these procedures.

With a flash period of for example 1 thousandth of a cycle Z, then 999 thousandths of a cycle period are available for analysis. The intensity difference between the white light signals and the fluorescence signals may accordingly be overcome by the difference in the observation time and the analysis time.

For the observer there then results during the whole cycle time an image with pseudo-white light. This may be transmitted onto a screen which shows a normal white light endoscopic picture. With this, a fluorescence diagnosis under white light is possible so that during the diagnosis, the simultaneous information of the optically indirect tumor sign and of the fluorescence tumor sign may be evaluated. This synergistic combination increases the diagnosis possibilities and makes it possible to recognise various cancer phenomena.

Figure 3:
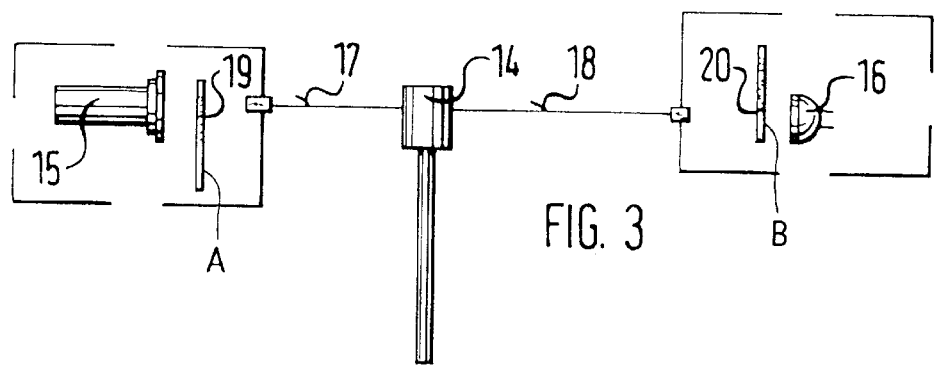

FIG. 3 shows an arrangement for diagnosis of malignant tissue by fluorescence observation, with an endoscope 14 which is coupled to a camera 15 and a flashlight source 16 by way of an optical fiber 17 or 18.

A filter system 19 in the form of the filter wheel A is allocated to the camera 15, whereas the flashlight source cooperates with a filter system 20 (filter wheel B).

Figure 4:
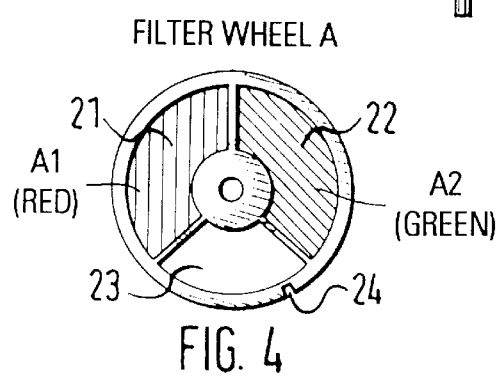
Figure 5:
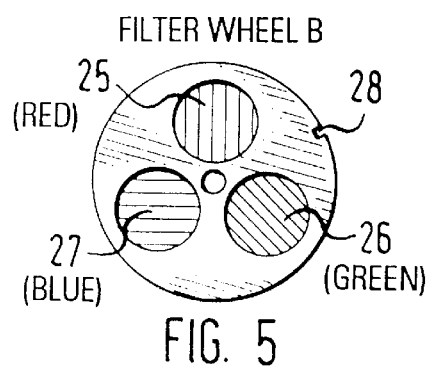

Filter wheel A and filter wheel B are explained in FIGS. 4 and 5.

The filter wheel A comprises a first filter 21, e.g. for red light (filter A1), and a second filter 22, e.g. for green light (filter A2). Furthermore an opening 23 and a coding slot 24 on the outer circumference of the filter wheel A are present. The coding slot 24 serves the sychronisation of the filter wheel A with the filter wheel B. A grey filter for intensity adaptation may be incorporated into the opening 23.

The filter wheel B is equipped with three round filters 25, 26 and 27 for the spectral colors red (R), green (G) and blue (B). By way of the signals RGB a pseudo-white light is composed. Filter wheel B is also provided with a coding slot 28.

The cooperation and the working principle of the arrangement described hereinafter is made clear by way of FIG. 6, in which the active (I) and inactive (O) phases of the indicated elements are represented with time lines.

With an image repetition frequency of a monitor of 50 Hz, the time t1=20 ms. During this time, five images are recorded by the camera 15. The first three pictures are the recordings of the flashes through the filters 25, 26 and 27 during time t3.

The flashlight source 16, the camera 15 as well as the filter systems 19, 20 are so synchronized that the camera 15 processes the optical signal just when a flash is created and the respective filters 25–27 arc located in front of the flashlight source 16. None of the color filters 21 or 22 are swung into the irradiation path in front of the camera 15 during this time.

With a maximum flash frequency of for example 1000 Hz, the time t3=3 ms. The filter wheel B must then turn at 20,000 r.p.m. For the measurement of the fluorescence there thus remains 17 ms. The analysis time is hereby divided into the collecting time for the red fluorescence and the collecting time for the green fluorescence. On taking account of the transition times from filter 21 to 22 of the filter wheel A, there still remains for the time t2 roughly 5 ms to 6 ms in each case.

Figure 7:
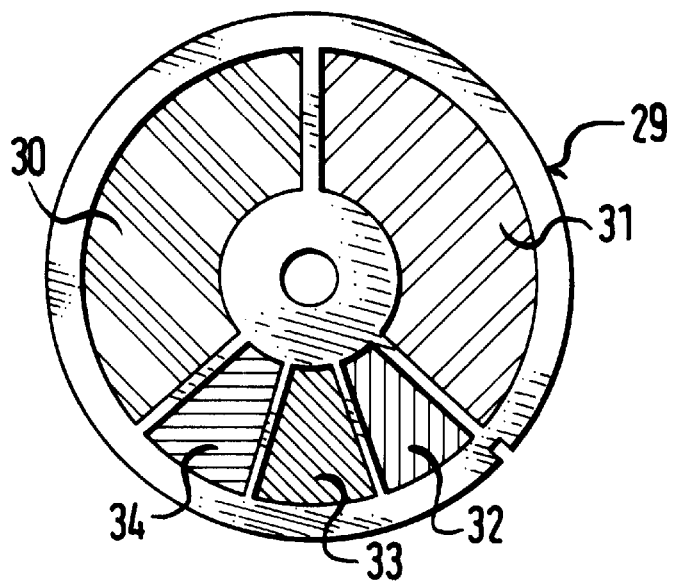

In FIG. 7, a filter wheel 29 is represented which likewise can be applied with an arrangement according to FIG. 3. In this case no filter system for the flashlight source is required. The filter wheel B is then dispensed with.

The filter wheel 29 comprises a measuring filter 30 and a second measuring filter 31 for the fluorescence measurement. For the white light observation the filters 32, 33 and 34 for the spectral colors red (R), green (G) and blue (B) are present.

Figure 6:
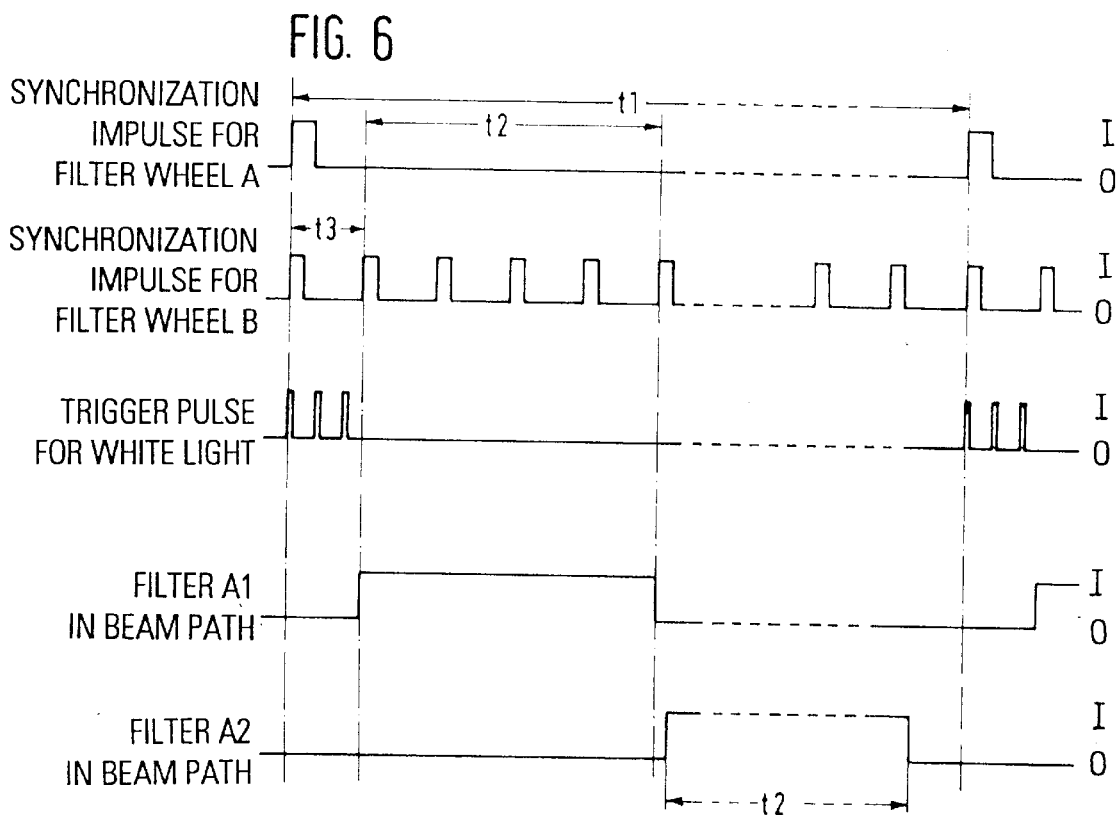

With such an arrangement the impulse diagram corresponds to that of FIG. 6, wherein the synchronization impulses from the filter wheel B are dispensed with, since this wheel is not present. The flash sequence of the flashlight source 16 is then synchronized such that the flashes are triggered in each case when a filter 32, 33 or 34 is in the irradiation path of the camera 16.

Figure 8:
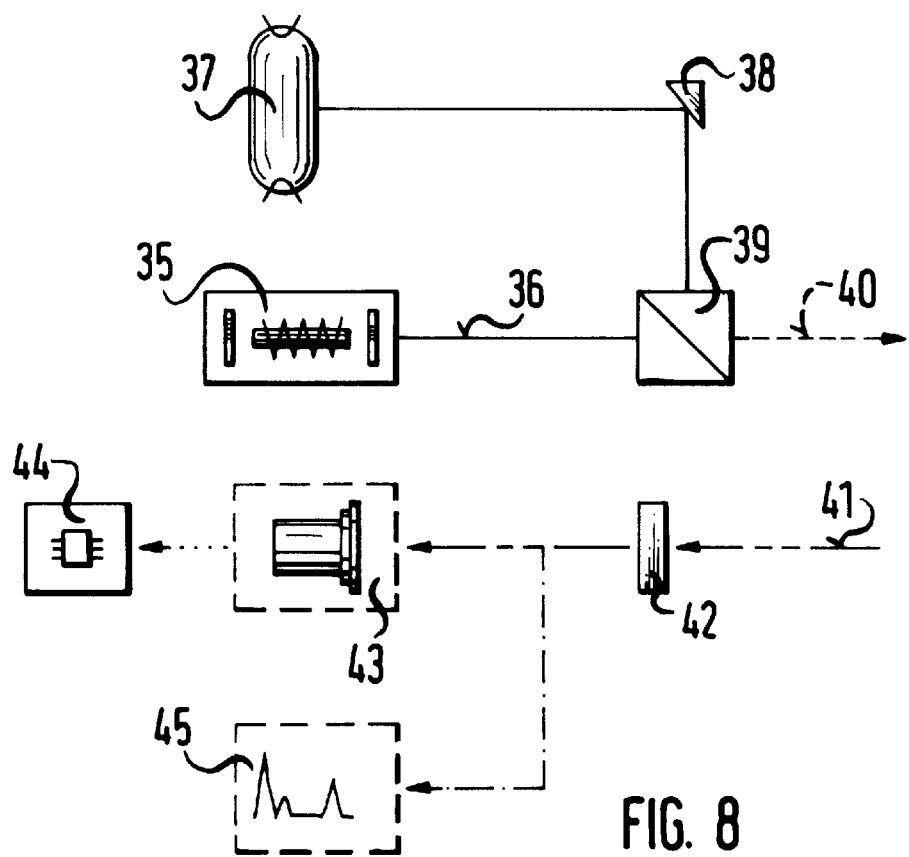

A further embodiment example of the invention is represented in FIG. 8.

A monochromatic light source is indicated at 35 and from which a constant light 36 in the blue spectral region with a wavelength of preferably 488 nm is emitted. The light component required for the simultaneous observation of the tissue to be observed with white light is produced by the flash tube 37.

With the help of a mirror 38, the light flashes are diverted and in the image separator, are coupled with the light phase 36 emitted from the light source 35. The beam 40 which is composed of the light components is then guided through an optical fiber not represented here onto the tissue to be examined by way of an endoscope.

From the tissue there results a light image reflection according to the beam indicated at 41, whereby this beam comprises a real light component and a fluorescence light component. These light components are separated in a RGB filter 42. With this, there results red-green-blue signals which are recorded by an image recording element 43 and, by way of a processor 44 allocated to this, are correspondingly evaluated.

As far as the image recording element 43 is concerned, this may be for instance be a highly sensitive black and white camera or a CCD chip.

Basically, a direct evaluation of the extracted signal may also take place in a spectrometer 45.

The RGB filter 42 and the processor 44 are synchronized so that in each case, corresponding to exactly that light component which is let through by the filter 42, a corresponding signal is recorded and evaluated by the processor in thc RGB modulation procedure. As a result, in total five signals are used, that is the three RGB signals as simulated white light, and the red and green component from the fluorescence light.

Here the video chip always remains sensitive. The reading time is regulated by the RGB filter 42, whereby the reading time during the analysis phase is divided into the fluorescence time red and the fluorescence time green. The white light part is low compared to the fluorescent light component so that one can exploit the sensitivity difference for analysis.

The application of a black and white camera has the advantage that it is not only much more inexpensive compared to a color camera, but is also considerably lighter and easier to handle. It may also be equipped with a light amplifier in order to further increase the sensitivity.

We claim:

1. An arrangement for diagnosing malignant tissue by fluorescence observation, comprising an endoscope (1), a white light source (3, 16, 37), a fluorescence stimulator (4, 35) for emitting a light beam, and an analyzer (5, 15, 43), wherein the fluorescence stimulator (4, 35) constantly emits a continuous light beam during a diagnosis, the white light source (3, 16, 37) comprises a device for effecting a periodic change of intensity of a visible light pulse emitted from the white light source (3, 16, 37), and the analyzer (5, 15, 43) is activated when the intensity of the visible light pulse approaches zero and is deactivated during emission of the visible light pulse.

2. The arrangement according to claim 1, wherein the white light source (3, 16, 37) comprises a stroboscope.

3. The arrangement according to claim 2, wherein the fluorescence stimulator (4) comprises a laser.

4. The arrangement according to claim 2, wherein the fluorescence stimulator comprises an arc lamp.

5. The arrangement according to claim 2, further comprising a filter (19, 42) arranged adjacent to the analyzer (5, 15, 43) for selectively blanking out a stimulation wavelength emitted from the fluorescence stimulator (4, 35).

6. The arrangement according to claim 1, wherein the fluorescence stimulator (4) comprises a laser.

7. The arrangement according to claim 6, further comprising a filter (19, 42) arranged adjacent to the analyzer (5, 15, 43) for selectively blanking out a stimulation wavelength emitted from the fluorescence stimulator (4, 35).

8. The arrangement according to claim 1, wherein the fluorescence stimulator comprises an arc lamp.

9. The arrangement according to claim 8, further comprising a filter (19, 42) arranged adjacent to the analyzer (5, 15, 43) for selectively blanking out a stimulation wavelength emitted from the fluorescence stimulator (4, 35).

10. The arrangement according to claim 1, further comprising a filter (19, 42) arranged adjacent to the analyzer (5, 15, 43) for selectively blanking out a stimulation wavelength emitted from the fluorescence stimulator (4, 35).

11. A method for diagnosing malignant tissue by fluorescence observation, comprising exposing a tissue to be observed to a continuous fluorescence stimulation by a light beam with a stimulation wavelength, simultaneously observing the tissue under light pulses (B) produced by a stroboscope (3, 16, 37), and analyzing a wavelength of fluorescence emitted from the tissue, wherein an analyzer (5, 15, 43) for conducting the analysis is deactivated during each of the light pulses (B) and is activated during a period of a dark phase (D) between two of the light pulses (B).

12. The method according to claim 11, wherein the wavelength emitted by the tissue (2) corresponds to the stimulation wavelength and is selectively blanked out before the analyzer (5, 15, 43).

* * * * *